US007429570B2

(12) United States Patent
Seidman et al.

(10) Patent No.: US 7,429,570 B2
(45) Date of Patent: *Sep. 30, 2008

(54) METHODS OF OPTIMIZING DRUG THERAPEUTIC EFFICACY FOR TREATMENT OF IMMUNE-MEDIATED GASTROINTESTINAL DISORDERS

(75) Inventors: Ernest G. Seidman, Côte St. Luc (CA); Yves Theoret, Montreal (CA)

(73) Assignee: Hopital Sainte-Justine, Montreal, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/689,472

(22) Filed: Mar. 21, 2007

(65) Prior Publication Data

US 2007/0197461 A1    Aug. 23, 2007

Related U.S. Application Data

(63) Continuation of application No. 11/420,694, filed on May 26, 2006, which is a continuation of application No. 11/152,866, filed on Jun. 14, 2005, now Pat. No. 7,105,497, which is a continuation of application No. 10/703,920, filed on Nov. 6, 2003, now Pat. No. 6,987,097, which is a continuation of application No. 10/034,456, filed on Dec. 27, 2001, now Pat. No. 6,680,302, which is a continuation of application No. 09/288,344, filed on Apr. 8, 1999, now Pat. No. 6,355,623.

(60) Provisional application No. 60/101,714, filed on Sep. 24, 1998.

(51) Int. Cl.
*A61K 31/70* (2006.01)
*A61K 31/52* (2006.01)
*A61K 31/415* (2006.01)

(52) U.S. Cl. ............................. 514/45; 514/46; 514/47; 514/48; 514/262; 514/391; 514/395

(58) Field of Classification Search ........................ None
See application file for complete search history.

(56) References Cited

U.S. PATENT DOCUMENTS

| 5,733,915 | A  | * | 3/1998 | Sandborn ................. 514/263.3 |
| 6,355,623 | B2 | * | 3/2002 | Seidman et al. ................ 514/45 |
| 6,680,302 | B2 | * | 1/2004 | Seidman et al. ................ 514/45 |
| 6,987,097 | B2 | * | 1/2006 | Seidman et al. ................ 514/45 |
| 7,105,497 | B2 | * | 9/2006 | Seidman et al. ................ 514/45 |
| 2001/0006970 | A1 | * | 7/2001 | Seidman et al. ............. 514/262 |
| 2002/0082239 | A1 |   | 6/2002 | Seidman et al. |

FOREIGN PATENT DOCUMENTS

WO    WO 96/30021    3/1996

OTHER PUBLICATIONS

|R| Sandborn (II), "Azathioprine: State of the Art in Inflammatory Bowel Disease," Scand. Journal Gastroenterology, 33(S225, Supplement 1), 92-99 (1998); Chemical Abstracts, 128(21), p. 8, Abstract No. 252417j (May 25, 1998).*
(S) Budavari et al.(eds.), The Merck Index, 11th Edition, Merck & Co., Rahway, NJ, 1989, only p. 916 supplied, see entry #918 (Azathioprine).*
(T) Berkow et al. (eds.), The Merck Manual of Diagnosis and Therapy, 16th Edition, Merck & Co., Rahway, NJ, 1992, only pp. 328-330, 826-828 and 830-845 supplied.*
(U) Sandborn et al., "Lack of Effect of Intravenous Administration on Time to Respond to Azathioprine for Steroid-Treated Crohn's Disease," Gastroenterology, 117(3), 527-535 (Sep. 1999).*
(V) Belaiche et al., "Therapeutic Drug Monitoring of Azathioprine and 6-Mercaptopurine Metabolites in Crohn Disease," Scandanavian Journal of Gastroenterology, 2001(1), 71-76.*
W) Bouhnik et al., "Long-term Follow-up of Patients with Crohn's Disease Treated with Azathioprine or 6-Mercaptopurine," The Lancet, 347, 215-219 (Jan. 27, 1996).*
(X) Keuzenkamp-Jansen et al., "Thioprine Methyltransferase: A Review and a Clinical Pilot Study," Journal of Chromatography B, 678, 15-22 (1996).*
(Y) Cuffari et al., "6-MP Metabolite Levels: A Potential Guide to Crohn's Disease Therapy," Gastroenterology, 113(2), 690-692 (Aug. 1997).*
Aarbakke et al. "Thiopurine biology and pharmacology." *Trends Pharmacol. Sci.* (1997), 18:3-7.
Andersen et al. Pharmacokinetics, dose adjustments, and 6-mercaptopurine/methotrexate drug interactions in two patients with thiopurine methyltransferase deficiency. *Acta Paediatr.* (1998), 87:108-111.
Balis et al. "Pharmacokinetics and pharmacodynamics of oral methotrexate and mercaptopurine in children with lower risk acute lymphoblastic leukemia: a joint children's cancer group and pediatric oncology branch study." *Blood* (1998), 92(10):3569-3577.
Bergan et al. "Monitored high-dose azathioprine treatment reduces acute rejection episodes after renal transplantation." *Transplantation* (1998), 66(3):334-339.
Bergen et al. Patterns of azathioprine metabolites in neutrophils, lymphocytes, retriculocytes, and erythrocytes: relevance to toxicity and monitoring in recipients of renal allografts. *Ther. Drug Monit.* (1997), 19:502-509.
Black et al. "Thiopurine methyltransferase genotype predicts therapy-limiting severe toxicity from azathioprine." *Annals of Internal Medicine* (1998), 129(9):716-718.
Bökkerink et al. "6-mercaptopurine: cytotoxicity and biochemical pharmacology in human malignant T-lymphoblasts." *Biochem. Pharm.* (1996), 45(7):1455-1463.
Bostrom et al. "Cellular pharmacology of 6-mercaptopurine in acute lymphoblastic leukemia." *The American Journal of Pediatric Hematology/Oncology* (1993), 15(1):80-86.

(Continued)

*Primary Examiner*—Shaojia Anna Jiang
*Assistant Examiner*—L. E. Crane
(74) *Attorney, Agent, or Firm*—Townsend and Townsend and Crew LLP

(57) ABSTRACT

The present invention provides a method of optimizing therapeutic efficacy and reducing toxicity associated with 6-mercaptopurine drug treatment of an immune-mediated gastrointestinal disorder such as inflammatory bowel disease. The method of the invention includes the step of determining the level of one or more 6-mercaptopurine metabolites in the patient having an immune-mediated gastrointestinal disorder.

45 Claims, 3 Drawing Sheets

OTHER PUBLICATIONS

Candy et al. "A controlled double blind study of azathioprine in the management of Crohn's disease." *Gut* (1995), 37:674-678.

Cattan et al. "6-Mercaptopurine pharmacokinetics and blood lymphocyte subpopulations in patients with Crohn's disease treated with azathioprine." *Gastroenterol. Clin. Biol.* (1998), 22:160-167.

Chan et al. "Azathioprine metabolism: pharmacokinetics of 6-mercaptopurine, 6-thiouric acid and 6-thioguanine nucleotides in renal transplant patients," *J. Clin. Pharmacol.* (1990), 30:358-363.

Chrzanowska et al. "Determination of 6-thioguanine and 6-methylmercaptopurine metabolites in renal transplantation recipients and patients with glomerulonephritis treated with azathioprine." *Ther. Drug Monit.* (1999), 21:231-237.

Colonna et al. "The role of leukopenia in the 6-mercaptopurine-induced remission of refractory Crohn's disease." *Amer. J. Gastroenterology* (1994), 89:362-366.

Connell et al. "Bone morrow toxicity caused by azathioprine in inflammatory bowel disease." *Gut* (1993), 34:1081-1085.

Coulthard et al. "The relationship between thiopurine methyltransferase activity and genotype in blasts from patients with acute leukemia." *Blood* (1998), 92(8):2856-2862.

Cuffari et al. "6-Mercaptopurine metabolism in Crohn's disease: correlation with efficacy and toxicity." *Gut* (1996), 39:401-406.

Cuffari et al. "Quantitation of 6-thioguanine in peripheral blood leukocyte DNA in Crohn's disease patients on maintenance 6-mercaptopurine therapy." *Can. J. Physiol. Pharmacol.* (1996), 74:580-585.

Dervieux et al. "A HPLC method for the monitoring of human red cell 6-thioguanine and methyl 6-mercaptopurine in a single run." *Purine and Pyrimidine Metabolism in Man IX* (1998), 140:729-734.

Dervieux et al. "Simultaneous determination of 6-thioguanine and methyl 6-mercaptopurine nucleotides of azathioprine in red blood cells by HPLC." *Clin. Chem.* (1998), 44(3):551-555.

Dubinsky et al. "6-MP metabolite levels predict clinical efficacy and drug toxicity in pediatric IBD." *J. Pediatr. Gastro. Nutr.* (1998), 27(4):465, abstract 9.

El-Gamel et al. "Effect of allopurinol on the metabolism of azathioprine in heart transplant patients." *Transplantation Proceedings* (1998), 30:1127-1129.

Erb et al. "Pharmacokinetics and metabolism of thiopurines in children with acute lymphoblastic receiving 8-thioguanine versus 6-mercaptopurine," *Cancer Chemother. Pharmacol.* (1998), 42:266-272.

Ganiere-Monteil et al. "Thiopurine methyl transferase activity: new extraction conditions for high-performance liquid chromatographic assay." *J. Chromatogr.-B* (1999), 727:235-239.

Giverhaug et al. "Increased concentrations of methylated 6-mercaptopurine metabolites and 6-thioguanine nucleotides in human leukemic cells in vitro by methotrexate." *Biochem. Pharmacol.* (1998), 55:1641-1646.

Goldstein et al. "Toxicities and infections associated with chronic 6-mercaptopurine (6-MP) use in Crohn's disease (CD): Do we need to discontinue treatment?" *Gastroenterology* (1998), 114(4):G4042.

Hawthorne et al. "Randomized controlled trial of azathioprine withdrawal in ulcerative colitis." *Br. Med. J.* (1992), 305:20-22.

Jacqz-Aigrain et al. "Thiopurine methyltransferase activity in a French population: h.p.l.c. assay conditions and effects of drugs and inhibitors." *Br. J. Clin. Pharmac.* (1994), 38:1-8.

Kirschner B. "Safety of azathioprine and 6-mercaptopurine in pediatric patients with inflammatory bowel disease." *Gastroenterology* (1998), 115(4):813-821.

Klemetsdal et al. "Identification of factors regulating thiopurine methyltransferase activity in a Norwegian population." *Eur. J. Clin. Pharmacol.* (1993), 44:147-152.

Kröplin et al. "Determination of thiopurine methyltransferase activity in erythrocytes using 6-thioguanine as the substrate." *Purine and Pyrimidine Metabolism in Man IX*, edited by Griesmacher et al., Plenum Press, New York (1998), 142:741-745.

Krynetski et al. "Cancer genetics '98, pharmacogenetics of cancer therapy: getting personal." *Am. J. Hum. Genet.* (1998), 63:11-16.

Lennard et al. "Variable 6-mercaptopurine metabolism and treatment outcome in childhood lymphoblastic leukemia." *J. Clin. Oncol.* (1989), 7(12):1816-1823.

Lennard et al. "Assay of 6-thioguanine nucleotide, a major metabolite of azathioprine, 6-mercaptopurine and 6-thioguanine, in human red blood cells." *J. Pharm. Pharmacol.* (1982), 35:15-18.

Lennard et al. "High-performance liquid chromatographic assay of the methyl and nucleotide metabolites of 6-mercaptopurine: quantitation of red blood cell 6-thioguanine nucleotide, 6-thioinosinic acid and 6-methylmercaptopurine metabolites in a single sample." *J. Chromatog.* (1992), 583:83-90.

Lennard et al. "High-performance liquid chromatographic assay of human red blood cell thiopurine methyltransferase activity." *J. Chromatog. B* (1994), 66(1):25-33.

Lennard et al. "Childhood leukaemia: a relationship between intracellular 6-Mercaptopurine metabolites and neutropenia." *Br. J. Clin. Pharmac.* (1983), 16:359-363.

Lennard et al. "Genetic variation in response to 6-mercaptopurine for childhood acute lymphoblastic leukaemia." *Lancet* (1990), 336:225-229.

Lennard et al. "Intracellular metabolites of mercaptopurine in children with lymphoblastic leukaemia: a possible indicator of non-compliance?" *Br. J. Cancer* (1995), 72(4):1004-1006.

Lennard et al. "Is 6-thioguanine more appropriate than 6-mercaptopurine for children with acute lymphoblastic leukaemia?" *Br. J. Cancer* (1993), 68:186-190.

Lennard et al. "Pharmacogenetics of acute azathioprine toxicity: relationship to thiopurine methyltransferase genetic polymorphism." *Clin. Pharmacol. Ther.* (1989), 46:149-154.

Lennard et al. "Thiopurine drugs in the treatment of childhood leukaemia: the influence of inherited thiopurine methyltransferase activity on drug metabolism and cytotoxicity." *Br. J. Clin. Pharmacol.* (1997), 44:455-461.

Lennard et al. "Thiopurine pharmacogenetics in leukemia: correlation of erythrocyte thiopurine methyltransferase activity and 6-thioguanine nucleotide concentrations." *Clin. Pharm. Ther.* (1987), 41(1):18-25.

Lennard, L. "Clinical Implications of Thiopurine Methyltransferase-Optimization of Drug Dosage and Potential Drug Interactions." *Ther. Drug. Monit.* (1998), 20(5):527-531.

Lennard, L. "The clinical pharmacology of 6-mercaptopurine." *Eur. J. Clin. Pharmacol.* (1992), 43:329-339.

Lilleyman et al. "Mercaptopurine metabolism and risk of relapse in childhood lymphoblastic leukaemia," *Lancet* (1994), 343:1188-1190.

Markowitz et al. "6-mercaptopurine (6-MP) + prednisone therapy for newly diagnosed pediatric Crohn's disease (CD): A prospective multicenter, placebo-controlled clinical trail." *Gastroenterol* (1998), 114(4):G4227.

Markowitz et al. "Immunosuppressive therapy in pediatric inflammatory bowel disease: results of a survey of the North American Society for Pediatric Gastroenterology and Nutrition. Subcommittee on immunosuppressive use of the Pediatric IBD Collaborative Research Forum." *Am. J. Gastroenterol.* (1993), 88(1):44-48.

Markowitz et al. "Long-term 6-mercaptopurine treatment in adolescents with Crohn's disease." *Gastroenterol* (1990), 99:1347-1351.

Markowitz et al. "Relationship of leukopenia to 6-MP induced remission of Crohn's disease," *J. Pediatr. Gastroenterol. Nutr.* (1998), 27(4):465, abstract 8.

McLeod et al. "Polymorphic thiopurine methyltransferase in erythrocytes in indicative of activity in leukemic blasts from children with acute lymphoblastic leukemia," *Blood* (1995), 85(7):1897-1902.

McLeod et al. "Thiopurine methyltransferase activity in American white subjects and black subjects." *Clin. Pharmacol. Ther.* (1994), 55:15-20.

Pearson et al. "Azathioprine and 6-mercaptopurine in Crohn disease, a meta-analysis." *Ann. Interm. Med.* (1995), 123(2):132-142.

Present et al. "6-Mercaptopurine in the management of inflammatory bowel disease: short- and long-term toxicity." *Annals of Internal Medicine* (1989), 111(8):641-649.

Present et al. "Treatment of Crohn's disease with 6-mercaptopurine: a long-term, randomized, double-blind study." *N. Engl. J. Med.* (1980), 302:981-987.

Rellling et al. "Prognostic importance of 6-mercaptopurine dose intensity in acute lymphoblastic leukemia," *Blood* (1999), 93(9):2817-2823.

Reynolds, *Martindale the extra pharmacopoeia*, The Pharmaceutical Press, London (1993), pp. 449-450.

Rosenberg et al. "A controlled trial of azathioprine in the management of chronic ulcerative colitis." *Gastroenterol*. (1975), 69:96-99.

Sandborn et al. "Measurement of thiopurine methyltransferase (TMPT) activity in patients with inflammatory bowel disease (IBD) does not predict side effects from treatment with 6-mercaptopurine (6-MP) or azathioprine." *Gastroenterology* (1993), 104(4)(2):A774.

Sandborn et al. "An intravenous loading dose of azathioprine decreases the time to respond in patients with Crohn's disease." *Gastroenterology* (1995), 109:1808-1817.

Sandborn, W. "A review of immune modifier therapy for inflammatory bowel disease: azathioprine, 6-mercaptopruine, cyclosporine, and methotrexate." *Amer. J. Gastroenterology* (1996), 91(3):423-433.

Sandborn, W. "6-MP metabolite levels: a potential guide to Crohn's disease therapy." *Gastroenterology* (1997), 113(2):690-692.

Schmiegelow et al. "6-Thioguanine nucleotide accumulation in red blood cells during maintenance chemotherapy for childhood acute lymphoblastic leukemia, and its relation to leukopenia." *Cancer Chemother. Pharmacol*. (1990), 26:288-292.

Schmiegelow et al. "Risk of relapse in childhood acute lymphoblastic leukemia is related to RBC methotrexate and mercaptopurine metabolites during maintenance chemotherapy." *J. Clin. Oncol*. (1995), 13(2):345-351.

Schütz et al. "Should 6-Thioguanine nucleotides be monitored in heart transplant recipients given azathioprine?" *Ther. Drug Monit*. (1996), 18:228-233.

Snow et al. "The role of genetic variation in thiopurine methyltransferase activity and the efficacy and/or side effects of azathioprine therapy in dermatologic patients." *Arch. Dermatol*. (1995), 131:193-197.

Van Os et al. "Azathioprine pharmacokinetics after intravenous, oral, delayed release oral and rectal foam administration." *Gut* (1996), 39:63-68.

Van Os et al. "Simultaneous determination of azathioprine and 6-mercaptopurine by high-performance liquid chromatography." *J. Chromatog. B* (1996), 679:147-154.

Vogt et al. "The importance of methylthio-IMP for methylmercaptopurine ribonucleoside (Me-MPR) cytotoxicity in Molt F4 human malignant T-lymphoblasts." *Biochimica et Biophysica Acta* (1993), 1181:189-194.

Warren et al. "Quantitation of 6-thioguanine residues in peripheral blood leukocyte DNA obtained from patients receiving 6-mercaptopurine-based maintenance therapy." *Cancer Res*. (1995), 55:1670-1674.

Welch et al. "Pharmacokinetics of mercaptopurine: plasma drug and red cell metabolite concentrations after an oral dose." *Ther. Drug Monit*. (1997), 19(4):382-385.

Willoughby et al. "Controlled trail of azathioprine in Crohn's disease." *Lancet* (1971), 731:944-947.

Zins et al. "A dose ranging study of azathioprine pharmacokinetics following single dose administration of a delayed release oral azathioprine formulation." *Gastroenterology* (1996), 110(4):A1054.

Zins et al. "A dose-ranging study of azathioprine pharmacokinetics after single-dose administration of a delayed-release oral formulation." *J. Clin. Pharmacol*. (1997), 37:38-46.

Zins et al. "Simultaneous determination of azathioprine and its metabolites in plasma using a high pressure liquid chromatography assay." *Gastroenterology* (1996), 110(4):A1054.

Dubinsky et al.; An Open-Label Pilot Study Using Thioguanine as a Therapeutic Alternative in Crohn's Disease Patients Resistant to 6-Mercaptopurine Therapy; *Inflammatory Bowel Disease*; (2001) 7(3):181-189.

Dubinsky et al.; 6-MP Metabolite Profiles Provide a Biochemical Explanation for 6-Mp Resistance in Patients with Inflammatory Bowel Disease; *Gastroenterology*; (2002) 122:904-915.

Juanita Brooks & Jonathan Singer; MML's Second Supplemental Response to Prometheus' First Set of Interrogatories, dated Jun. 1, 2006; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

Juanita Brooks & Jonathan Singer; Mayo Medical Laboratories' Fifth Supplemental Response to Prometheus' Second Set of Interrogatories (No. 13), dated Nov. 17, 2006; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

Juanita Brooks & Jonathan Singer; "Defendant Mayo Medical Laboratories' Second Amended Answer to Second Amended Complaint and Second Amended Counterclaims, Demand for Jury Trial" dated Oct. 3, 2006; submitted in Civil Action No. 04 CV 1200 JAH (RHB) titled *Prometheus Laboratories, Inc. v. Mayo Collaborative Services dba Mayo Medical Laboratories*, and *Mayo Clinic Rochester*.

Juanita Brooks & Jonathan Singer; MML's Ninth Supplemental Response to Prometheus' Interrogatory No. 2, dated Nov. 17, 2006; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

Juanita Brooks & Jonathan Singer; Defendants' Supplemental Invalidity Contentions Pursuant to Court Orders of Nov. 2, 2006, and Jan. 8, 2007, with Exhibits A-M, dated Jan. 18, 2007; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

Juanita Brooks & Jonathan Singer; "Defendants' Memorandum of Points and Authorities in Support of Their Motion for Summary Judgment of Patent Invalidity Under 35 U.S.C. § 101;" dated Jan. 29, 2007; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

F.T. Alexandra Mahaney, et al.; Prometheus Laboratories, Inc.'s Opposition to Defendants' Motion for Summary Judgment of Patent Invalidity Under 35 U.S.C. § 101 and exhibits A-C; dated Feb. 28, 2007; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

Juanita Brooks & Jonathan Singer; "Defendants' Reply in Support of Their Motion for Summary Judgment of Patent Invalidity;" dated Mar. 9, 2007; submitted in Civil Action No. 04 CV 1200 JAH (RBB) titled *Prometheus Laboratories, Inc. v. Mayo Collaborative Services dba Mayo Medical Laboratories*, and *Mayo Clinic Rochester*.

Prometheus Laboratories, Inc. v. Mayo Colloborative Services, et al.; Civil No. 04cv1200 JAH (RBB); (1) Order Granting Defendants' Motion for Summary Judgement of Patent Invalidity Pursuant to 35 U.S.C. § 101, etc.; issued by the Honorable John A. Houston, U.S. District Court for the Southern District of California on Mar. 28, 2008.

Cuffari et al., "Utilisation of erythrocyte 6-thioguanine metabolite levels to optimize azathioprine therapy in patients with inflammatory bowel disease." *Gut* 2001; 48:642-646.

\* cited by examiner

METHODS OF OPTIMIZING DRUG THERAPEUTIC EFFICACY FOR TREATMENT OF IMMUNE-MEDIATED GASTROINTESTINAL DISORDERS

The present application is a continuation of U.S. application Ser. No. 11/420,694, filed May 26, 2006, which is a continuation of U.S. application Ser. No. 11/152,866, filed Jun. 14, 2005, now U.S. Pat. No. 7,105,497, which is a continuation of U.S. application Ser. No. 10/703,920, filed Nov. 6, 2003, now U.S. Pat. No. 6,987,097, which is a continuation of U.S. application Ser. No. 10/034,456, filed Dec. 27, 2001, now U.S. Pat. No. 6,680,302, which is a continuation of U.S. application Ser.No. 09/288,344, filed Apr. 8, 1999, now U.S. Pat. No. 6,355,623, which claims priority to U.S. Provisional Application No. 60/101,714, filed Sep. 24, 1998, each of which is herein incorporated by reference in its entirety for all purposes.

BACKGROUND OF THE INVENTION

The present invention relates generally to autoimmunity and immune-mediated gastrointestinal disorders such as inflammatory bowel disease and more specifically to methods for optimizing treatment of immune-mediated gastrointestinal disorders.

BACKGROUND INFORMATION

Immune-mediated gastrointestinal disorders encompass a wide range of debilitating gastrointestinal diseases of various etiologies. One such immune-mediated gastrointestinal disorder, inflammatory bowel disease (IBD), is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe and in ulcerative colitis often is accompanied by bleeding. Anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

6-Mercaptopurine (6-MP) and azathioprine (AZA), a prodrug that is non-enzymatically converted to 6-mercaptopurine (6-MP), are 6-MP drugs that can be used as an effective treatment for inflammatory bowel diseases such as Crohn's disease and ulcerative colitis (Kirschner *Gastroenterology* 115:813-821 (1998)). 6-MP can be enzymatically converted to various 6-MP metabolites, including 6-methyl-mercaptopurine (6-MMP) and 6-thioguanine (6-TG) and their nucleotides. 6-TG nucleotides are thought to be the active metabolite in mediating many of the effects of 6-MP drug treatment.

Thiopurine methyltransferase (TPMT) is a cytoplasmic enzyme that preferentially catalyzes the S-methylation of 6-MP and 6-TG to form S-methylated metabolites such as 6-MMP and 6-methylthioguanine (6-MTG), respectively. TPMT exhibits genetic polymorphism, with 89% of Caucasians and African Americans having high activity, 11% intermediate activity and 1 in 300 TPMT deficient. Clinical studies with AZA and 6-MP have shown an inverse relationship between TPMT activity and 6-TGN accumulation. Patients who less efficiently methylate these thiopurines have more extensive conversion to 6-TGN, which can lead to potentially fatal hematopoietic toxicity. Therefore, patients who have less active TPMT can be more susceptible to toxic side effects of 6-MP therapy.

Although drugs such as 6-MP and AZA have been used for treating IBD, non-responsiveness and drug toxicity unfortunately complicate treatment in some patients. Complications associated with 6-MP drug treatment include allergic reactions, neoplasia, opportunistic infections, hepatitis, bone marrow suppression, and pancreatitis. Therefore, many physicians are reluctant to treat patients with AZA because of its potential side effects, especially infection and neoplasia.

Thus, there exists a need to develop methods to optimize the dose of 6-mercaptopurine drugs and assess biotransformation in individual patients to optimize the therapeutic efficacy of 6-mercaptopurine drugs while minimizing toxic side effects. The present invention satisfies this need and provides related advantages as well.

SUMMARY OF THE INVENTION

The present invention provides a method of optimizing therapeutic efficacy of 6-mercaptopurine drug treatment of an immune-mediated gastrointestinal disorder. The method includes the steps of administering a 6-mercaptopurine drug to a subject having an immune-mediated gastrointestinal disorder; and determining a level of 6-thioguanine in the subject having the immune-mediated gastrointestinal disorder, where a level of 6-thioguanine less than a level corresponding to about 230 pmol per $8 \times 10^8$ red blood cells indicates a need to increase the amount of 6-mercaptopurine drug subsequently administered to the subject and where a level of 6-thioguanine greater than a level corresponding to about 400 pmol per $8 \times 10^8$ red blood cells indicates a need to decrease the amount of 6-mercaptopurine drug subsequently administered to the subject. The methods are directed to treating immune-mediated gastrointestinal disorders, including inflammatory bowel diseases (IBD) such as Crohn's disease and ulcerative colitis, lymphocytic colitis, microscopic colitis, collagenous colitis, autoimmune enteropathy, allergic gastrointestinal disease and eosinophilic gastrointestinal disease. In a method of optimizing therapeutic efficacy of 6-mercaptopurine treatment of IBD, the subject having IBD can be, for example, a pediatric subject. The level of 6-thioguanine can be determined, for example, in red blood cells using high pressure liquid chromatography.

The present invention also provides a method of reducing toxicity associated with 6-mercaptopurine drug treatment of an immune-mediated gastrointestinal disorder. The method of reducing toxicity associated with an immune-mediated gastrointestinal disorder includes the steps of administering a 6-mercaptopurine drug to a subject having the immune-mediated gastrointestinal disorder; and determining a level of a 6-mercaptopurine metabolite in the subject having the immune-mediated gastrointestinal disorder, where a level of the 6-mercaptopurine metabolite greater than a predetermined toxic level of the 6-mercaptopurine metabolite indicates a need to decrease the amount of 6-mercaptopurine drug subsequently administered to the subject, thereby reducing toxicity associated with 6-mercaptopurine drug treatment of the immune-mediated gastrointestinal disorder. In a method of the invention, the 6-mercaptopurine metabolite can be, for example, 6-thioguanine and the predetermined toxic level of 6-thioguanine can correspond, for example, to a level of about 400 pmol per $8\times10^8$ red blood cells. Where the elevated 6-mercaptopurine metabolite is 6-thioguanine, the toxicity associated with 6-mercaptopurine treatment can be, for example, hematologic toxicity. The 6-mercaptopurine metabolite also can be a metabolite such as 6-methyl-mercaptopurine and the predetermined toxic level of 6-methyl-mercaptopurine can correspond, for example, to a level of about 7000 pmol per $8\times10^8$ red blood cells. Where the elevated 6-mercaptopurine metabolite is 6-methyl-mercaptopurine, the toxicity associated with 6-mercaptopurine treatment can be, for example, hepatic toxicity.

Further provided by the invention is a method of optimizing therapeutic efficacy and reducing toxicity associated with 6-mercaptopurine drug treatment of an immune-mediated gastrointestinal disorder. The method includes the steps of administering a 6-mercaptopurine drug to a subject having an immune-mediated gastrointestinal disorder; determining a level of 6-thioguanine in the subject having the immune-mediated gastrointestinal disorder; and determining a level of 6-methyl-mercaptopurine in the subject having the immune-mediated gastrointestinal disorder, where a level of 6-thioguanine less than a predetermined minimal therapeutic level indicates a need to increase the amount of 6-mercaptopurine drug subsequently administered to the subject, thereby increasing therapeutic efficacy; where a level of 6-thioguanine greater than a predetermined toxic level of 6-thioguanine indicates a need to decrease the amount of 6-mercaptopurine drug subsequently administered to the subject, thereby reducing toxicity associated with 6-mercaptopurine treatment of the immune-mediated gastrointestinal disorder; and where a level of 6-methyl-mercaptopurine greater than a predetermined toxic level of 6-methyl-mercaptopurine indicates a need to decrease the amount of 6-mercaptopurine drug subsequently administered to the subject, thereby reducing toxicity associated with 6-mercaptopurine treatment of the immune-mediated gastrointestinal disorder.

In such a method of optimizing therapeutic efficacy and reducing toxicity associated with 6-mercaptopurine drug treatment of an immune-mediated gastrointestinal disorder, the predetermined minimal therapeutic level of 6-thioguanine can be, for example, a level corresponding to about 230 pmol per $8\times10^8$ red blood cells; the predetermined toxic level of 6-thioguanine can be, for example, a level corresponding to about 400 pmol per $8\times10^8$ red blood cells; and the predetermined toxic level of 6-methyl-mercaptopurine can be, for example, a level corresponding to about 7000 pmol per $8\times10^8$ red blood cells. The level of 6-thioguanine and 6-methyl-mercaptopurine each can be conveniently determined, for example, in red blood cells using high pressure liquid chromatography. The invention further provides methods to optimize the therapeutic efficacy of 6-mercaptopurine drug treatment of a non-IBD autoimmune disease.

DETAILED DESCRIPTION OF THE INVENTION

The present invention provides a method of optimizing therapeutic efficacy of 6-mercaptopurine (6-MP) drug treatment of an immune-mediated gastrointestinal disorder. The method includes the steps of administering a 6-MP drug to a subject having an immune-mediated gastrointestinal disorder; and determining a level of 6-thioguanine (6-TG) in the subject having the immune-mediated gastrointestinal disorder, where a level of 6-TG less than a level corresponding to about 230 pmol per $8\times10^8$ red blood cells indicates a need to increase the amount of 6-MP drug subsequently administered to the subject and where a level of 6-TG greater than a level corresponding to about 400 pmol per $8\times10^8$ red blood cells indicates a need to decrease the amount of 6-MP drug subsequently administered to the subject. The methods are directed to treating immune-mediated gastrointestinal disorders, including inflammatory bowel diseases (IBD) such as Crohn's disease and ulcerative colitis, lymphocytic colitis, microscopic colitis, collagenous colitis, autoimmune enteropathy, allergic gastrointestinal disease and eosinophilic gastrointestinal disease. In a method of optimizing therapeutic efficacy of 6-MP treatment of IBD, the subject having IBD can be, for example, a pediatric subject. The level of 6-TG can be determined, for example, in red blood cells using high pressure liquid chromatography (HPLC).

The invention provides methods of optimizing therapeutic efficacy of 6-MP drug treatment of an immune-mediated gastrointestinal disorder. The methods of the invention are particularly useful for treating an immune-mediated gastrointestinal disorder such as IBD, including Crohn's disease and ulcerative colitis and subtypes thereof. The methods of the invention allow the clinician to provide an individually optimized dosage of a 6-MP drug so as to achieve a target level of a 6-MP metabolite in a particular patient having an immune-mediated gastrointestinal disorder, thereby optimizing the effectiveness of 6-MP drug therapy in the patient. The methods of the invention for optimizing therapeutic efficacy of 6-MP drug treatment involve determining the level of 6-TG in a patient having an immune-mediated gastrointestinal disorder. As disclosed herein, the level of 6-TG measured in a patient treated with a 6-MP drug was an indicator of the effectiveness of drug treatment. A level of at least 230 pmol 6-TG/$8\times10^8$ red blood cells (RBC) was found in responders to drug therapy (see Examples I and II). These results indicate that determining the level of 6-TG can be used to assess whether a patient has a level of 6-TG that is sufficient to alleviate symptoms of an immune-mediated gastrointestinal disorder such as IBD, thus optimizing therapeutic efficacy.

Figure 1:
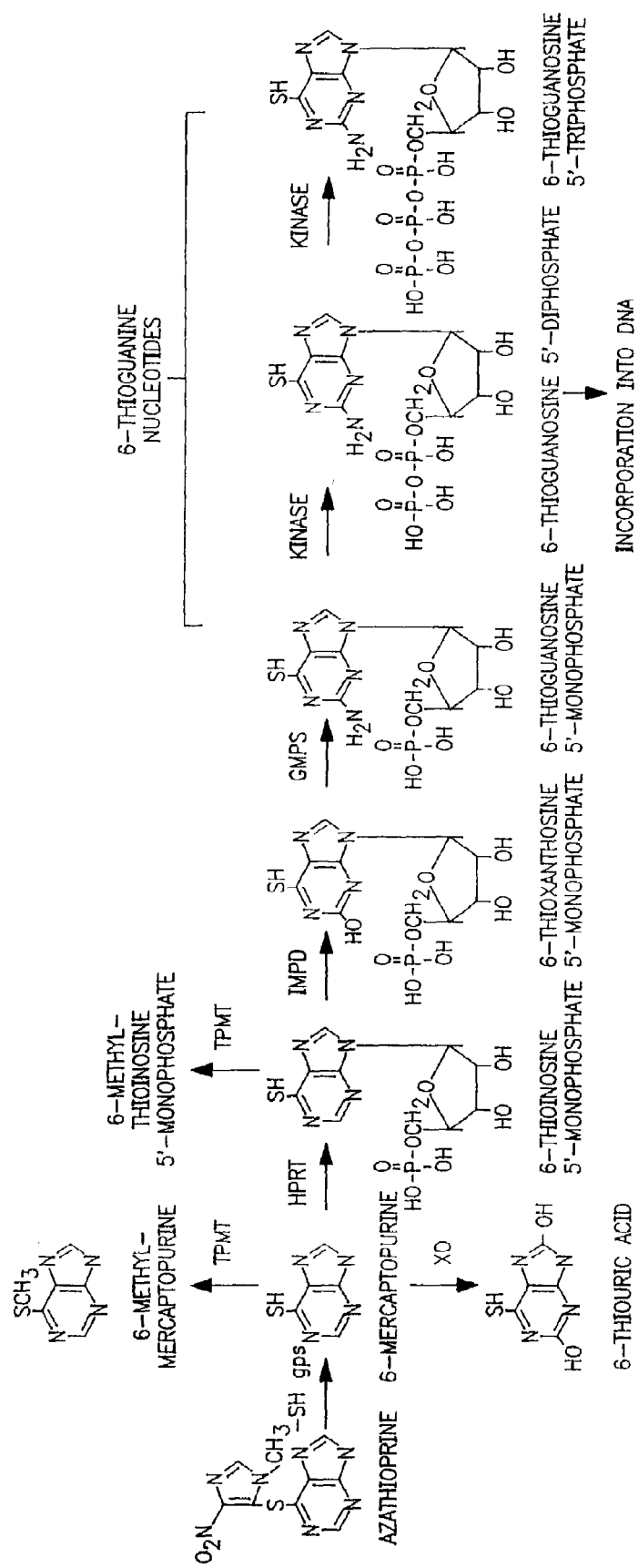
FIG. 1 shows mercaptopurine metabolism and the structures of 6-mercaptopurine (6-MP) metabolites. The initial metabolism of 6-MP is catalyzed by thiopurine methyltransferase (TPMT), xanthine oxidase (XO), and hypoxanthine phosphoribosyltransferase (HPRT). Further metabolism of the thionucleotide is catalyzed by inosine monophosphate dehydrogenase (IMPD) and guanosine monophosphate synthetase (GMPS). The breakdown of azathioprine to 6-mercaptopurine is nonenzymatic.

As used herein, the term "6-mercaptopurine drug" or "6-MP drug" refers to any drug that can be metabolized to an active 6-mercaptopurine metabolite that has therapeutic efficacy such as 6-TG. Exemplary 6-mercaptopurine drugs as defined herein include 6-mercaptopurine (6-MP) and azathioprine (AZA). As illustrated in FIG. 1, both of 6-MP and AZA can be metabolized to 6-mercaptopurine metabolites such as the exemplary 6-mercaptopurine metabolites shown in FIG.

1, including 6-thioguanine (6-TG), 6-methyl-mercaptopurine (6-MMP) and 6-thiouric acid. (Lennard, *Eur. J. Clin. Pharmacol.* 43:329-339 (1992)).

Figure 2:
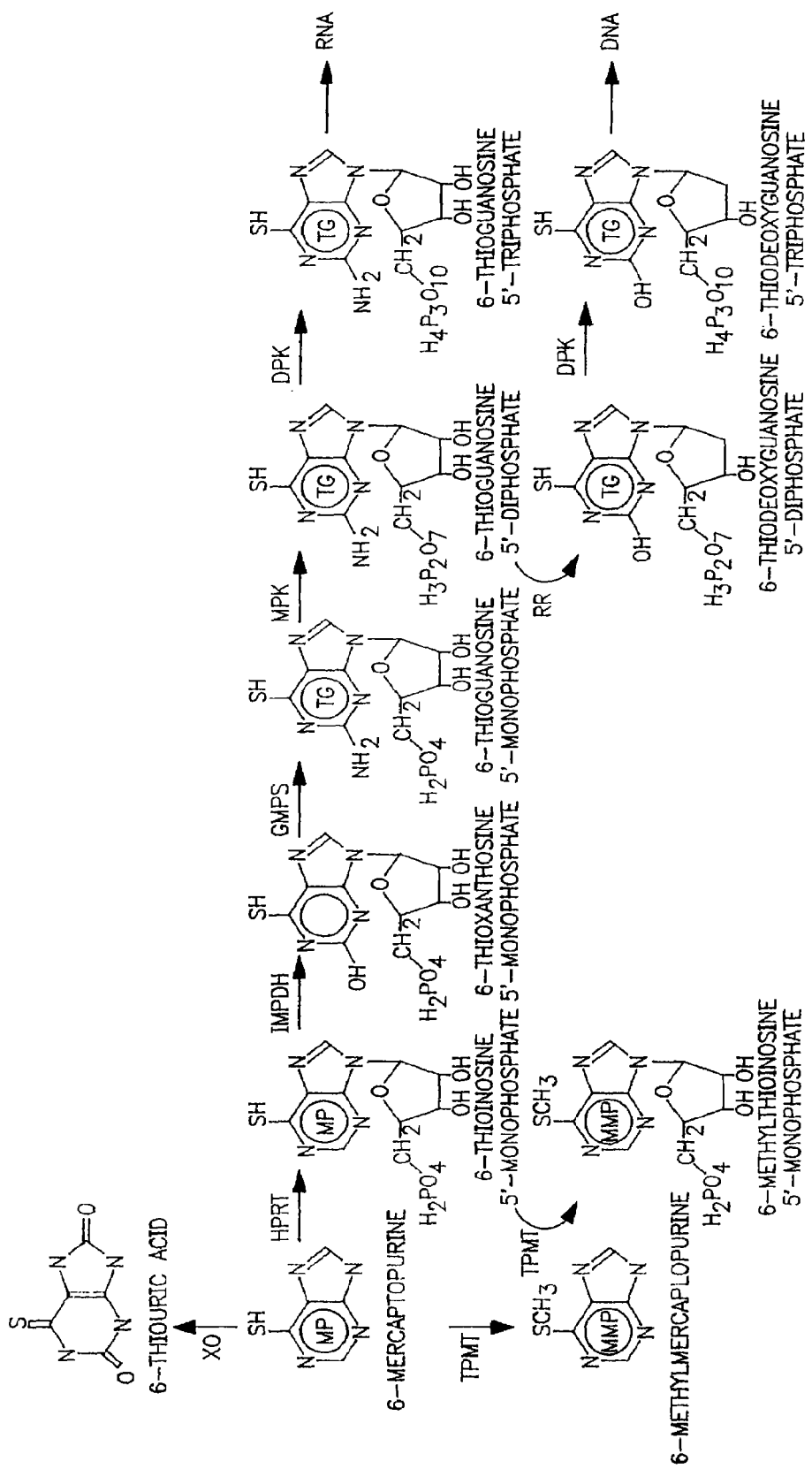
FIG. 2 shows 6-mercaptopurine (6-MP) metabolism and the 6-MP metabolites that are measured as 6-MP, 6-thioguanine (6-TG) and 6-methyl-mercaptopurine (6-MMP) (indicated as "MP," "TG" and "MMP" inside the base). 6-TG mono-phosphate is converted to the di- and tri-phosphate by monophosphate kinase (MPK) and diphosphate kinase (DPK), respectively. The ribonucleoside diphosphate is converted to deoxyribonucleoside diphosphate by ribonucleotide reductase (RR).

Other 6-MP drugs include, for example, 6-methylmercaptopurine riboside and 6-TG (Loo et al., *Clin. Pharmacol. Ther.* 9:180-194 (1968); O'Dwyer et al., *J. Natl. Cancer Inst.* 83:1235-1240 (1991); Erb et al., *Cancer Chemother. Pharmacol.* 42:266-272 (1998); Lancaster et al., *Br. J. Haematol.* 102:439-443 (1998); Ingle et al., *Am. J. Clin. Oncol.* 20:69-72 (1997); Evans and Relling, *Leuk. Res.* 18:811-814 (1994)). 6-TG is a particularly useful 6-MP drug in patients having high TPMT activity. Patients exhibiting high TPMT activity are expected to more easily convert 6-MP drugs such as 6-MP and AZA to 6-MMP (see FIGS. 1 and 2). As disclosed herein, high levels of 6-MMP are associated with hepatotoxicity (see Examples I and II). Therefore, patients with high TPMT activity can be more susceptible to toxic effects of 6-MP drug therapy. By administering 6-TG, which is an active 6-MP metabolite associated with therapeutic efficacy (see Examples I and II), the toxicity that can be associated with conversion of 6-MP to 6-MMP is bypassed.

It is understood that the 6-MP metabolites can be the metabolites shown in FIG. 1 or analogues thereof. As used herein, the term "6-thioguanine" or "6-TG" refers to 6-thioguanine or analogues thereof, including molecules having the same base structure, for example, 6-thioguanine ribonucleoside, 6-thioguanine ribonucleotide mono-, di- and tri-phosphate, 6-thioguanine deoxyribonucleoside and 6-thioguanine deoxyribonucleotide mono-, di, and triphosphate. The term "6-TG" also includes derivatives of 6-thioguanine, including chemical modifications of 6-TG, so long as the structure of the 6-TG base is preserved.

As used herein, the term "6-methyl-mercaptopurine" or "6-MMP" refers to 6-methyl-mercaptopurine or analogues thereof, including analogues having the same base structure, for example, 6-methyl-mercaptopurine ribonucleoside, 6-methyl-mercaptopurine ribonucleotide mono-, di-, and tri-phosphate, 6-methyl-mercaptopurine deoxyribonucleoside, and 6-methyl-mercaptopurine deoxyribonucleotide mono-, di- and tri-phosphate. The term "6-MMP" also includes derivatives of 6-methyl-mercaptopurine, including chemical modifications of 6-MMP, so long as the structure of the 6-MMP base is preserved.

The methods of the invention relate to treatment of an immune-mediated gastrointestinal disorder. As used herein, the term "immune-mediated gastrointestinal disorder" or "immune-mediated GI disorder" refers to a non-infectious disease of the gastrointestinal tract or bowel that is mediated by the immune system or cells of the immune system. Immune-mediated gastrointestinal disorders include, for example, inflammatory bowel diseases (IBD) such as Crohn's disease and ulcerative colitis, lymphocytic colitis, microscopic colitis, collagenous colitis, autoimmune enteropathy, allergic gastrointestinal disease and eosinophilic gastrointestinal disease.

The methods of the invention are particularly useful for treating IBD, or subtypes thereof, which has been classified into the broad categories of Crohn's disease and ulcerative colitis. As used herein, "a subject having inflammatory bowel disease" is synonymous with the term "a subject diagnosed with having an inflammatory bowel disease," and means a patient having Crohn's disease or ulcerative colitis. Crohn's disease (regional enteritis) is a disease of chronic inflammation that can involve any part of the gastrointestinal tract. Commonly, the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also includes complications such as inflammation of the eye, joints and skin; liver disease; kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. Some Crohn's disease cases display the typical discrete granulomas, while others show nonspecific transmural inflammation. As a result, the presence of discrete granulomas is indicative of CD, although the absence of granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994)).

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, supra, 1994).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease.

In addition to IBD, immune-mediated GI disorders also include other gastrointestinal diseases such as lymphocytic colitis; microscopic colitis; collagenous colitis; autoimmune enteropathy, including autoimmune enteritis and autoimmune enterocolitis; allergic gastrointestinal disease; and eosinophilic gastrointestinal disease, including eosinophilic gastroenteritis and eosinophilic enteropathy.

Over the past two decades, the histological evaluation of colorectal biopsies obtained by colonoscopy has expanded the spectrum of chronic IBD. A new group of immune-mediated bowel disorders has emerged, characterized by chronic watery diarrhea, minimal or absent endoscopic findings, and inflammatory changes in mucosal biopsies. Lymphocytic colitis, also commonly referred to as microscopic colitis, is a clinicopathological syndrome characterized primarily by lymphocytic infiltration of the epithelium. Collagenous colitis is defined by the presence of a collagenous band below the surface epithelium, accompanied by an increase in inflammatory cell infiltrate (Lazenby et al. *Hum. Pathol.* 20:18-28 (1989)). These disorders are often associated with other autoimmune diseases such as rheumatoid arthritis, pernicious anemia, thyroiditis, uveitis and type I diabetes mellitus. Clinicians have used immunosuppressive drugs, including 6-MP, to treat these disorders (Deslandres et al. *J. Pediatr. Gastroenterol. Nutr.* 25:341-346 (1997)).

Autoimmune enteropathy, including autoimmune enteritis and autoimmune enterocolitis, is a syndrome of severe secretory diarrhea and marked enterocolitis, in association with diagnostic circulating antibodies to enterocytes (Seidman et al., *J. Pediatr.* 117:929-932 (1990)). This syndrome, most often seen in infancy, can be seen in association with other autoimmune diseases. Complete villous atrophy is associated with a severe inflammatory reaction on small bowel biopsies. Although some cases remit after an extended period of time, most patients die without immunosuppressive therapy, which can include 6-MP drug therapy.

Eosinophilic gastrointestinal disease, including eosinophilic gastroenteritis and eosinophilic enteropathy, is characterized by a dense infiltration of eosinophils in one or more areas of the gastrointestinal tract, variable intestinal symptoms, and usually a peripheral eosinophilia (80% of cases). Food allergic, including allergic gastrointestinal disease, and eosinophilic disorders of the gastrointestinal tract are commonly treated by dietary elimination of the offending nutrients. However, both food induced and eosinophilic enteropathies may, in certain circumstances, require corticosteroid and immunosuppressive therapy, including 6-MP (Russo et al., *Pediatric Dev. Path.* 2:65-71 (1999)).

The methods of the invention relate to optimizing therapeutic efficacy of 6-MP drug treatment of an immune-mediated GI disorder, including IBD such as Crohn's disease and ulcerative colitis and subtypes thereof. The methods of the invention are particularly useful for treating patients dependent on steroid therapy for maintenance of remission of disease in Crohn's disease and ulcerative colitis patients. As used herein, the phrase "optimizing therapeutic efficacy of 6-MP drug treatment" refers to adjusting the therapeutic dosage of a 6-MP drug such as 6-MP or azathioprine so that the concentration of a 6-MP metabolite that is correlated with effective treatment is maintained. As set forth above, the methods of the invention allow the clinician to provide an individually optimized dosage of a 6-MP drug so as to achieve a target level of a 6-MP metabolite in a particular patient, thereby optimizing the effectiveness of 6-MP drug therapy in the patient. Therapeutic efficacy generally is indicated by alleviation of one or more signs or symptoms associated with the disease. In the case of immune-mediated GI disorders, in particular IBD, therapeutic efficacy is indicated by alleviation of one or more signs or symptoms associated with the disease, including, for example, joint pain, arthritis, arthalgia, anorexia, growth failure, fistula closure, abdominal pain, diarrhea, recurrent fever, anemia, weight loss, rectal bleeding, inflammation of the intestine, and loose discharges of blood, pus and mucus. Methods for determining therapeutic efficacy, in particular for treating IBD, are disclosed herein in Examples I and II.

Therapeutic efficacy can be readily determined by one skilled in the art as the alleviation of one or more signs or symptoms of the disease being treated. In the case of IBD, patients can be analyzed using a Crohn's disease activity index (Best et al., *Gastroenterology* 70:439-444 (1976)). IBD patients can also be analyzed using a Harvey-Bradshaw index (HBI)(Harvey and Bradshaw, *Lancet* 1:514 (1980)). The Harvey-Bradshaw index provides an analytical method for measuring signs or symptoms of Crohn's disease, including the signs or symptoms of general well-being, abdominal pain, number of liquid stools per day, abdominal mass, and complications such as arthralgia, uveitis, erythema nodosum, aphthous ulcers, pyoderma gangrenosum, anal fissure, new fistula and abscess. The Harvey-Bradshaw index is particularly useful when evaluating pediatric patients.

Previous studies suggested that measurement of 6-MP metabolite levels can be used to predict clinical efficacy and tolerance to azathioprine or 6-MP (Cuffari et al., *Gut* 39:401-406 (1996a)). However, it was unknown what concentrations of 6-MP metabolites correlated with optimized therapeutic efficacy or with toxicity (Cuffari et al., supra, 1996a). As disclosed herein, levels of 6-MP metabolites such as 6-TG and 6-MMP were determined and correlated with therapeutic efficacy and toxicity associated with 6-MP drug-therapy (see Examples I and II).

The invention is directed to methods of optimizing therapeutic efficacy of 6-MP drug treatment of an immune-mediated GI disorder by monitoring predetermined levels associated with therapeutic efficacy or toxicity and adjusting the 6-MP drug dosage so as to maintain an optimized dose that is efficacious and has reduced toxicity. The methods involve administering a 6-MP drug such as 6-MP or azathioprine to a subject having an immune-mediated GI disorder and determining a level of a 6-MP metabolite in the subject having the immune-mediated GI disorder. The methods of the invention are advantageous in that the dosage of a 6-MP drug can be adjusted to maximize the efficacy of treating an immune-mediated GI disorder such as IBD while minimizing toxicity associated with 6-MP drug treatment.

As used herein, the term "6-mercaptopurine metabolite" refers to a product derived from 6-mercaptopurine in a biological system. Exemplary 6-mercaptopurine metabolites are shown in FIG. 1 and include 6-thioguanine-(6-TG), 6-methyl-mercaptopurine (6-MMP) and 6-thiouric acid and analogues thereof. For example, 6-MP metabolites include 6-TG bases such as 6-TG, 6-thioguanosine mono-, di- and tri-phosphate; 6-MMP bases such as 6-methyl-mercaptopurine and 6-methyl-thioinosine monophosphate; 6-thioxanthosine (6-TX) bases such as 6-thioxanthosine mono-phosphate; 6-thioruric acid (6-TUA); and 6-MP bases such as 6-mercaptopurine and 6-thioinosine monophosphate (see FIG. 2). The immunosuppressive properties of 6-MP are believed to be mediated via the intracellular transformation of 6-MP to its active metabolites such as 6-TG and 6-MMP nucleotides. Furthermore, 6-MP metabolites such as 6-TG and 6-MMP were found to correlate with therapeutic efficacy and toxicity associated with 6-MP drug treatment of IBD patients (see Examples I and II).

The level of a 6-MP metabolite can be determined by methods well known in the art including, for example, those described in Lilleyman and Lennard, *Lancet* 343:1188-1190 (1994); Lennard and Singleton, *J. Chromatography Biomed. Applicat.* 583:83-90 (1992); Lennard and Singleton, *J. Chromatography* 661:25-33 (1994); and Cuffari et al., *Can. J. Physiol. Pharmacol.* 74:580-585 (1996b)). 6-MP metabolites such as 6-TG and 6-MMP can be measured, for example, by collecting red blood cells and extracting thiobases, for example, 6-MP, 6-TG, 6-TX and 6-MMP, which are released by acid hydrolysis. 6-MMP is converted to a form extractable by phenyl mercury salts (Dervieux and Boulieu, *Clin. Chem.* 44:2511-2525 (1998); Duchesne et al., *Proc. Amer. Soc. Clin. Oncol.* 13:137 (1994a); Duchesne et al., *Can. J. Physiol. Pharmacol.* 72:197 (1994b)). Such an analysis measures the thiobase and its analogues, including ribonucleoside, ribonucleotide, deoxyribonucleoside, deoxyribonucleotide thiobases as well as mono-, di- and tri-phosphate analogues, which have been converted to thiobases.

Acid hydrolyzed extracts can be analyzed by resolving 6-MP metabolites and measuring their levels. For example, HPLC such as reverse phase HPLC is a useful method for resolving and measuring the levels of 6-MP metabolites, including 6-MP, 6-TG and 6-MMP (Lennard and Singleton, supra, 1992). Ultraviolet light (UV) detection can be used to measure the 6-MP metabolites. A particularly useful method of measuring 6-MP metabolites is isocratic reverse phase HPLC with UV detection (Cuffari et al., supra, 1996b).

Other methods for measuring 6-MP metabolites can also be used. For example, ion-pairing HPLC with dual UV-wavelength detection can be used to measure 6-MP metabolites (Zimm and Strong, *Anal. Biochem.* 160:1-6 (1987)). Additional methods for measuring 6-MP metabolites include, for example, capillary electrophoresis with laser-induced fluorescence detection (Rabel et al., *Anal. Biochem.* 224:315-322 (1995)); anion exchange chromatography and fluorescent detection (Tidd and Dedhar *J. Chromatography* 145:237-246 (1978)); lanthanum precipitation, acid hydrolysis, back extraction and fluorometric assay (Fletcher and Maddocks, *Brit. J. Clin. Pharmacol.* 10:287-292 (1980)); thin layer chromatography (Bennet and Allen, *Cancer Res.* 31:152-158 (1971)); precolumn derivatization with the thiol-reactive fluorophore monobromobimane, treatment with alkaline phosphatase, HPLC resolution and quantification by fluorometry (Warren and Slordal, *Anal. Biochem.* 215:278-283 (1993)); and enzymatic hydrolysis followed by HPLC separation and UV detection (Giverhaug et al., *Ther. Drug Monit.* 19:663-668 (1997)). 6-MP metabolites such as 6-TG can also be measured in DNA by degrading DNA to deoxyribonucleosides, derivatizing deoxy-6-TG with a fluorophore and resolving on reverse phase HPLC (Warren et al., *Cancer Pes.* 55:1670-1674 (1995)).

As used herein, the level of a 6-MP metabolite can include the 6-MP metabolite itself, or the level of the 6-MP metabolite and analogues thereof. For example, as described above, acid hydrolysis can be used to release thionucleotides from a sample, resulting in conversion of mono-, di- and tri-phosphates to thiobases. In such an analysis, the level of several analogues of a thionucleotide are measured (see FIG. 2). For example, measuring 6-TG can include 6-thioguanosine 5'-mono-, di-, and tri-phosphate, and 6-thiodeoxyguanosine 5'-di-, and tri-phosphate. Measuring 6-MP can include 6-mercaptopurine and 6-thioinosine 5'-monophosphate. Measuring 6-MMP can include 6-methylmercaptopurine and 6-methylthioinosine 5'-monophosphate, and can also include 6-methylthioinosine di- and tri-phosphate, as well as 6-methyl thioguanosine.

A particularly useful determination of the level of a 6-MP metabolite is the median level of the 6-MP metabolite since the distribution of 6-MP metabolite values is trimodal. Unless otherwise designated, the levels referred to herein are median levels. A 6-MP metabolite level can also be a mean level, if so desired. Unless otherwise designated, the levels of 6-MP metabolites referred to herein are values per $8 \times 10^8$ RBC, whether reported as mean or median values.

6-MP metabolite levels can be conveniently assayed using red blood cells because such cells are readily available from the patient, lack a nucleus and are easy to manipulate. However, it should be understood that any measurement that allows determination of 6-MP metabolite levels can be used. For example, leukocytes can be used to measure 6-MP metabolite levels, which can be correlated with 6-MP metabolite levels in erythrocytes (Cuffari et al., supra, 1996b). Regardless of the method employed to measure 6-MP metabolites, one skilled in the art can readily measure 6-MP metabolite levels in a sample, for example, in leukocytes or DNA obtained from a patient, and correlate the level of 6-MP metabolites to the values disclosed herein, which were determined using RBC.

For convenience, levels of 6-MP metabolites disclosed herein are given in terms of an assay with RBC and, therefore, are given as an amount of a 6-MP metabolite in a given number of RBCs. 6-MP metabolites assayed in RBCs can also be determined relative to the amount of hemoglobin. However, it should be understood that one skilled in the art can measure 6-MP metabolite levels in samples other than RBCs and readily correlate such levels with 6-MP metabolite levels in RBCs. For example, one skilled in the art can readily determine levels of a 6-MP metabolite in cells such as leukocytes, or cells from the oral mucosa, and in RBCs by measuring the level of 6-MP metabolites in both types of cells and determining the correspondence between levels of 6-MP metabolites in RBCs and the levels in the other cells. Once a correspondence between 6-MP metabolites in RBCs and in a sample has been determined, one skilled in the art can use that correspondence to measure levels in the other sample and correlate those levels with the levels in RBCs disclosed herein.

As disclosed herein, the level of 6-TG in an IBD patient treated with a 6-MP drug was found to correlate with therapeutic efficacy (see Examples I and II). In particular, a median level of 230 pmol 6-TG/$8 \times 10^8$ RBC or more was found in IBD patients who responded to 6-MP drug therapy. Thus, as disclosed herein, a level of at least about 230 pmol 6-TG per $8 \times 10^8$ RBC can be a minimal therapeutic level of 6-TG for efficaciously treating a patient. Accordingly, a level of 6-TG below about 230 pmol/$8 \times 10^8$ RBC indicates a need to increase the amount of a 6-MP drug administered to the patient. A minimal therapeutic level of 6-TG for efficaciously treating a patient also can be, for example, at least about 240 pmol per $8 \times 10^8$ RBC; at least about 250 pmol per $8 \times 10^8$ RBC; at least about 260 pmol per $8 \times 10^8$ RBC; at least about 260 mol per $8 \times 10^8$ RBC or at least about 300 pmol per $8 \times 10^8$ RBC. It is understood that the minimal therapeutic levels of 6-TG disclosed herein are useful for treating immune-mediated gastrointestinal disorders, including IBD, as well as non-IBD autoimmune diseases.

The methods of the invention directed to determining whether a patient has a minimal therapeutic level of a 6-MP metabolite are useful for indicating to the clinician a need to monitor a patient for therapeutic efficacy and to adjust the 6-MP drug dose, as desired. For example, in a patient having less than a minimal therapeutic level of a 6-MP metabolite such as 6-TG and who also presents as unresponsive to 6-MP drug therapy or having poor responsiveness to 6-MP drug therapy as measured by minimal or no effect on a sign or symptom of the disease being treated, one skilled in the art can determine that the dosage of a 6-MP drug should be increased. However, if it is determined that a patient has less than a predetermined minimal therapeutic level of a 6-MP metabolite but is responsive to 6-MP therapy, the current dose of 6-MP drug can be maintained. Based on measuring 6-MP metabolite levels and assessing the responsiveness of the patient to 6-MP therapy, one skilled in the art can determine whether a 6-MP drug dose should be maintained, increased, or decreased.

Although 6-MP drugs such as 6-MP and azathioprine can be used for effective treatment of an immune-mediated GI disorder, including IBDs such as Crohn's disease or ulcerative colitis, administration of such drugs can be associated with toxic side effects. Toxicities associated with 6-MP drug administration include pancreatitis, bone marrow depression, allergic reactions and drug hepatitis as well as neoplasms and infectious complications (Present et al., *Annals Int. Med.* 111:641-649 (1989); Cuffari et al., supra, 1996a). As disclosed herein, various toxicities associated with 6-MP drug treatment, including hepatic toxicity, pancreatic toxicity and hematologic toxicity, correlate with the level of 6-MP metabolites in a subject administered a 6-MP drug (see Examples I and II).

Thus, the present invention also provides a method of reducing toxicity associated with 6-MP drug treatment of an immune-mediated GI disorder. The method of the invention for reducing toxicity associated with 6-MP drug treatment includes the steps of administering a 6-MP drug to a subject having an immune-mediated GI disorder; and determining a level of a 6-MP metabolite in the subject having the immune-mediated GI disorder, where a level of the 6-MP metabolite greater than a predetermined toxic level of the 6-MP metabolite indicates a need to decrease the amount of 6-MP drug subsequently administered to the subject, thereby reducing toxicity associated with 6-MP drug treatment of the immune-mediated GI disorder. In a method of the invention, the 6-MP metabolite can be, for example, 6-TG and the predetermined toxic level of 6-TG can correspond, for example, to a level of about 400 pmol per $8 \times 10^8$ red blood cells. Where the elevated 6-MP metabolite is 6-TG, the toxicity associated with 6-MP treatment can be, for example, hematologic toxicity, including leukopenia or bone marrow suppression. The 6-MP metabolite also can be a metabolite such as 6-MMP, and the predetermined toxic level of 6-MMP can correspond, for example, to a level of about 7000 pmol per $8 \times 10^8$ red blood cells. Where the elevated 6-MP metabolite is 6-MMP, the toxicity associated with 6-MP drug treatment can be, for example, hepatic toxicity.

As disclosed herein, the level of a 6-MP metabolite can be determined in a subject treated with a 6-MP drug and compared to a predetermined toxic level of a 6-MP metabolite such as 6-TG or 6-MMP to adjust future 6-MP drug administration, thereby reducing toxicity in the subject. For example, as disclosed herein, levels of 6-TG above about 400 pmol/$8 \times 10^8$ RBC indicated that a patient was likely to experience toxicity, in particular hematologic toxicity such as leukopenia (see Examples I and II). Accordingly, a level of 6-TG above about 400 pmol/$8 \times 10^8$ RBC can be a predetermined toxic level of 6-TG, which indicates that the amount of 6-MP drug subsequently administered should be decreased.

It is understood that, when a patient is determined to have a level of a 6-MP metabolite such as 6-TG or 6-MMP higher than a predetermined toxic level, one skilled in the art can make a determination as to whether a 6-MD drug dose should be decreased. For example, if the level of a 6-MP metabolite such as 6-TG or 6-MMP is higher than a predetermined toxic level, one skilled in the art can monitor for toxic side effects by measuring one or more of the toxicities associated with 6-MP drug treatment, as disclosed herein. As disclosed herein, a level of 6-TG greater than about 400 pmol per $8 \times 10^8$ RBCs was associated with increased risk of leukopenia or bone marrow suppression. Therefore, one skilled in the art can measure white blood cells (WBC) in a patient having levels of 6-TG higher than a predetermined toxic level to determine if the patient is exhibiting signs of reduced WBC counts. If such a patient exhibits signs of leukopenia or bone marrow suppression, the 6-MP drug dose can be reduced. However, if it is determined that a patient has levels of a 6-MP metabolite higher than a predetermined toxic level but does not exhibit signs of leukopenia or other 6-MP drug toxicities, one skilled in the art can determine that the current 6-MP drug dose can be maintained. Based on measuring 6-MP metabolite levels and determining signs or symptoms of toxicities associated with 6-MP drug treatment, one skilled in the art can determine whether a 6-MP drug dose should be maintained or decreased. As such, a level of a 6-MP metabolite higher than a predetermined toxic level can indicate a need to measure a toxicity associated with 6-MP drug treatment such as measuring WBCs or any of the other signs or symptoms of toxicities associated with 6-MP drug treatment to determine if the 6-MP drug dose should be adjusted.

Furthermore, it is understood that, when decreasing the 6-MP drug dose, one skilled in the art will know or can readily determine whether the 6-MP drug dose should be decreased to a lower dose or whether 6-MP drug administration should be stopped for some period of time, or terminated. For example, if the clinician determines that 6-MP drug therapy should be stopped for some period of time due to levels of a 6-MP metabolite exceeding a level predetermined to be toxic, the levels of 6-MP metabolites can be monitored after stopping 6-MP drug therapy until the level of the toxic 6-MP metabolite returns to a safe, non-toxic level. At that time, the clinician can resume 6-MP drug therapy, if desired.

The methods of the invention for reducing toxicity associated with 6-MP drug treatment of a disease involve comparing a level of a 6-MP metabolite to a predetermined toxic level of a 6-MP metabolite. In general, a "predetermined toxic level" of a 6-MP metabolite means a level of a 6-MP metabolite that has been correlated with one or more toxicities associated with 6-MP drug treatment. As disclosed herein, a predetermined toxic level of 6-TG can be about 400 pmol per $8 \times 10^3$ RBC. A predetermined toxic level of 6-TG also can be about 350 pmol per $8 \times 10^3$ RBC; 370 pmol per $8 \times 10^3$ RBC; 390 pmol per $8 \times 10^8$ RBC; 425 pmol per $8 \times 10^8$ RBC; or 450 pmol per $8 \times 10^8$ RBC. It is understood that the predetermined toxic levels of 6-TG disclosed herein are useful for treating immune-mediated GI disorders, including IBD, as well as non-IBD autoimmune diseases.

Another 6-MP metabolite useful for predicting the likelihood of toxicity is 6-methyl-mercaptopurine (6-MMP). As disclosed herein, a level of greater than about 7000 pmol 6-MMP/$8 \times 10^8$ in patients administered a 6-MP drug was associated with toxicity, in particular hepatotoxicity (see Examples I and II). These results indicate that the level of 6-MMP can be used to predict toxicity in a patient treated with a 6-MP drug. As disclosed herein, a predetermined toxic level of 6-MMP can be about 7000 pmol per $8 \times 10^8$ RBC. A predetermined toxic level of 6-MMP also can be about 6000 pmol per $8 \times 10^8$ RBC; 6500 pmol per $8 \times 10^8$ RBC; 7500 pmol per $8 \times 10^8$ RBC; or 8000 pmol per $8 \times 10^5$ RBC. It is understood that the predetermined toxic levels of 6-MMP disclosed herein are useful for treating immune-mediated GI disorders, including IBD, as well as non-IBD autoimmune diseases. According to a method of the invention, if the level of 6-MMP is above a predetermined toxic level, the subsequent administration of a 6-MP drug can be decreased to minimize toxicity.

Further provided by the invention is a method of optimizing therapeutic efficacy and reducing toxicity associated with 6-MP drug treatment of an immune-mediated GI disorder such as IBD. The method includes the steps of administering a 6-MP drug to a subject having an immune-mediated GI disorder; determining a level of 6-TG in the subject having the immune-mediated GI disorder; and determining a level of 6-MMP in the subject having the immune-mediated GI disorder, where a level of 6-TG less than a predetermined minimal therapeutic level indicates a need to increase the amount of 6-MP drug subsequently administered to the subject, thereby increasing therapeutic efficacy; where a level of 6-TG greater than a predetermined toxic level of 6-TG indicates a need to decrease the amount of 6-MP drug subsequently administered to the subject, thereby reducing toxicity associated with 6-MP treatment of the immune-mediated GI disorder; and where a level of 6-MMP greater than a predetermined toxic level of 6-MMP indicates a need to decrease the amount of 6-MP drug subsequently administered to the subject, thereby reducing toxicity associated with 6-MP drug treatment of the immune-mediated GI disorder.

In such a method of optimizing therapeutic efficacy and reducing toxicity associated with 6-MP drug treatment of an immune-mediated GI disorder such as IBD, the predetermined minimal therapeutic level of 6-TG can be, for example, a level corresponding to about 230 pmol per $8 \times 10^8$ red blood cells; the predetermined toxic level of 6-TG can be, for example, a level corresponding to about 400 pmol per $8 \times 10^8$ red blood cells; and the predetermined toxic level of 6-MMP can be, for example, a level corresponding to about 7000 pmol per $8 \times 10^8$ red blood cells. In a method of the invention, the subject having an immune-mediated GI disorder such as IBD can be, for example, a pediatric subject. The level of 6-TG and 6-MMP each can be conveniently determined, for example, in red blood cells using HPLC.

The methods of the invention are useful for optimizing the amount of a 6-MP drug to be administered to a patient with an immune-mediated GI disorder such as IBD. By measuring the levels of 6-MP metabolites such as 6-MMP and 6-TG, one skilled in the art can determine the 6-MP drug dosage that will result in optimized therapeutic efficacy and reduced toxicity when administered to a patient.

As disclosed herein, gender and age differences were observed in pediatric patients treated with 6-MP drug therapy (see Example III). Very little change in 6-MP metabolite levels of 6-TG and 6-MMP was seen for girls who had gone through puberty (older than age 12). However, boys who had gone through puberty (older than age 14) had a marked decrease in the level of 6-MMP, suggesting that hormonal changes occurring during puberty can affect the metabolism of a 6-MP drug. Therefore, the methods of the invention can additionally be used to monitor 6-MP metabolite levels in adolescents, particularly those going through puberty, in order to optimize therapeutic efficacy or minimize toxic side effects associated with 6-MP therapy.

As disclosed herein, TPMT genotyping is useful for predicting the effectiveness of 6-MP therapy in an IBD patient (see Example IV). Heterozygote patients are expected to have lower TPMT activity and should therefore be monitored for high levels of 6-TG for possible toxic levels associated with leukopenia or bone marrow suppression. 6-MP drug doses can be reduced accordingly. Wild type homozygous patients are expected to have higher TPMT activity and should therefore be monitored to maintain an effective therapeutic level of 6-TG and to determine if patients develop toxic levels of 6-MMP. Homozygous patients deficient in TPMT activity can be treated with lower doses of a 6-MP drug provided that patients are closely monitored for toxicity such as leukopenia. Therefore, TPMT genotyping can be used to predict patient responsiveness to and potential toxicities associated with 6-MP drug therapy. Furthermore, TPMT genotyping can be combined with other methods of the invention to both determine TPMT genotype and to monitor 6-MP metabolites. TPMT genotyping can be particularly valuable when determining a starting dose of 6-MP drug therapy but can also be useful when adjusting 6-MP drug doses after therapy has begun.

The invention additionally provides a method of optimizing therapeutic efficacy of 6-MP drug treatment of a non-IBD autoimmune disease. The method includes the steps of administering a 6-MP drug to a subject having a non-IBD autoimmune disease; and determining a level of 6-thioguanine (6-TG) in the subject having the non-IBD autoimmune disease, where a level of 6-TG less than a minimal therapeutic level indicates a need to increase the amount of 6-MP drug subsequently administered to the subject and where a level of 6-TG greater than a predetermined toxic level indicates a need to decrease the amount of 6-MP drug subsequently administered to the subject. The level of 6-MMP can also be monitored in a patient having a non-IBD autoimmune disease to determine if the level is higher than a predetermined toxic level of 6-MMP.

The methods of the invention can be used to optimize therapeutic efficacy of 6-MP drug treatment of a non-IBD autoimmune disease. Such a non-IBD autoimmune disease can be any non-IBD autoimmune disease treatable by a 6-MP drug such as 6-MP or azathioprine and, in particular, can be a disease such as rheumatoid arthritis, systemic lupus erythematosus, autoimmune hepatitis (chronic active hepatitis) or pemphigus vulgaris.

As used herein, the term "non-IBD autoimmune disease" means a disease resulting from an immune response against a self tissue or tissue component, including both self antibody responses and cell-mediated responses. The term non-IBD autoimmune disease encompasses organ-specific non-IBD autoimmune diseases, in which an autoimmune response is directed against a single tissue, including myasthenia gravis, vitiligo, Graves' disease, Hashimoto's disease, Addison's disease, autoimmune gastritis, and Type I diabetes mellitus. The term non-IBD autoimmune disease also encompasses non-organ specific autoimmune diseases, in which an autoimmune response is directed against a component present in several or many organs throughout the body. Non-organ specific autoimmune diseases include, for example, systemic lupus erythematosus, progressive systemic sclerosis and variants, polymyositis and dermatomyositis, and rheumatoid disease. Additional non-IBD autoimmune diseases include pernicious anemia, primary biliary cirrhosis, autoimmune thrombocytopenia, and Sjögren's syndrome. One skilled in the art understands that the methods of the invention can be applied to these or other non-IBD autoimmune diseases treatable by a 6-MP drug such as 6-MP or azathioprine, or other 6-MP drugs, as desired. Specifically excluded from the term "non-IBD autoimmune disease" are diseases resulting from a graft versus host response and inflammatory bowel diseases such as Crohn's disease or ulcerative colitis.

The methods of the invention are also useful for treating a non-immune-mediated GI disorder autoimmune disease. As used herein, the term "non-immune-mediated GI disorder autoimmune disease" is a non-IBD autoimmune disease and specifically excludes immune-mediated GI disorders.

The methods of the invention can be particularly useful for optimizing therapeutic efficacy of 6-MP drug treatment of rheumatoid arthritis. Rheumatoid arthritis is a chronic systemic disease primarily of the joints, usually polyarticular, marked by inflammatory changes in the synovial membranes and articular structures and by muscle atrophy and rarefaction of the bones.

The methods of the invention also can be particularly valuable for optimizing therapeutic efficacy of 6-MP drug treatment of lupus erythematosus and, in particular, systemic lupus erythematosus (SLE). Systemic lupus erythematosus is a chronic, remitting, relapsing inflammatory, and sometimes febrile multisystemic disorder of connective tissue. SLE can be acute or insidious at onset and is characterized principally by involvement of the skin, joints, kidneys and serosal membranes.

Autoimmune hepatitis, also called chronic active hepatitis, also can be treated with a 6-MP drug and the dose optimized using the methods of the invention. Autoimmune hepatitis is a chronic inflammation of the liver occurring as a sequel to hepatitis B or non-A, non-B hepatitis and is characterized by infiltration of portal areas by plasma cells and macrophages, piecemeal necrosis, and fibrosis.

The methods of the invention also can be useful for treating pemphigus vulgaris, the most common and severe form of pemphigus, which is a chronic, relapsing and sometimes fatal skin disease characterized clinically by the development of successive crops of vesicles and bullae and treated by azathioprine. This disorder is characterized histologically by acantholysis, and immunologically by serum autoantibodies against antigens in the intracellular zones of the epidermis.

The methods of the invention can also be used to optimize the therapeutic efficacy of 6-MP drug treatment of graft versus host disease, which can occur in transplant patients. Graft versus host disease occurs when a transplant patient has an immune reaction to the non-self transplant organ or tissue. The methods of the invention for optimizing the therapeutic efficacy of 6-MP drug treatment is particularly useful for treating heart, kidney and liver transplant recipients. The methods of the invention can be used to optimize therapeutic efficacy and/or minimize toxicity associated with 6-MP drug treatment of a transplant patient.

The following examples are intended to illustrate but not limit the present invention.

EXAMPLE I

6-Mercaptopurine Metabolite Levels Predict Clinical Efficacy and Drug Toxicity in Pediatric IBD This example describes measuring 6-MP metabolite levels and correlation with the response of IBD patients treated with a 6-MP drug.

The levels of the 6-MP metabolites 6-TG and 6-MMP were measured in IBD patients to whom 6-MP pro-drug was administered, and the relationship of 6-MP metabolites to clinical disease activity and drug toxicity was determined. Briefly, blood was sampled (n=89) prior to daily administration of 6-MP in 55 IBD patients (CD n=51, UC n=4) receiving 1-1.5 mg/kg/day over at least a 4 month period ($\geq$4 mo.). When AZA was administered, a conversion factor of 2.07 was used to convert to the equivalent 6-MP dose. Twice as much AZA is administered relative to 6-MP to have an equivalent dose of 6-MP.

Erythrocyte 6-TG, 6-MMP and 6-MP thiobases were measured (pmol/$8 \times 10^8$ RBC) using reverse phase HPLC. Briefly, blood samples were collected in EDTA (ethylene diamine tetraacetic acid) as anticoagulant. Cells were centrifuged and washed three times with an equal volume of 0.9% saline. Washed packed cells were stored at $-70°$ C. until analysis was performed.

For acid hydrolysis, 500 µl deionized $H_2O$, 50 µl thawed red blood cells, 4.0 µl of the appropriate standard or control, 500 µl 3.0 N $H_2SO_4$, and 300 µl 10 mM dithiothreitol (DTT) was added to an 8 ml glass screw cap tube. The capped tubes were placed in a heating block preheated to 100° C. and hydrolyzed. For 6-MMP, hydrolysis was carried out for 5 hours. For 6-MP and 6-TG, hydrolysis was carried out for 1 hour. After the incubation, tubes were cooled in a room temperature water bath. To tubes hydrolyzed for 5 hours (6-MMP), 400 µl 3.4 N NaOH and 1.0 ml 2 M Tris buffer, pH 9.0 was added. To tubes hydrolyzed for 1 hour. (6-MP/6-TG), 450 µl 3.4 N NaOH and 500 µl 2M Tris base was added. A volume of 4 ml 0.03% phenylmercuric chloride in methylene chloride was added to each tube. The tubes were capped and lightly agitated on a bi-directional rotator (15 min for 6-MMP and 30 min for 6-MP/6-TG). The contents were transferred to a 15 ml polypropylene centrifuge tube and centrifuged at 3500 rpm for 3 min at 10° C. The aqueous phase (top layer) was discarded, and 3.0 ml of the organic phase (bottom layer) was transferred to a clean 15 ml polypropylene centrifuge tube. The analytes in the organic phase were back extracted by adding 225 µl 0.1 N HCl and lightly mixing on an orbital rotator for 5 min. Following vortexing for 30 seconds, the tubes were centrifuged at 3500 rpm for 3 min at 10° C.

For 6-MMP analysis, 50 µl analyte was analyzed on a C18 reverse phase column with the mobile phase containing 1 mM DTT, 2.078% triethylamine and 4% methanol, adjusted to pH 3.2 with concentrated $H_3PO_4$. For 6-MP and 6-TG analysis, 100 µl analyte was analyzed on a C18 reverse phase column using 0.1 M $H_3PO_4$ and 1 mM DTT in $H_2O$ as the mobile phase.

Hepatic, pancreatic and hematological tests were obtained every 3 months. Clinical remission was defined as a Harvey Bradshaw Index <5 in those patients off corticosteroids or weaned to a level of prednisone $\leq$0.4 mg/kg/od (administered every other day). Treatment failures were defined as non-responders (HBI >5 or steroid dependence) or cessation of 6-MP due to side effects.

As shown in Table 1, a 6-TG level of >225 pmol per $8 \times 10^8$ RBC was associated with remission. The median values shown in the tables represent pmol of the indicated 6-MP metabolite per $8 \times 10^8$ RBC. Excessive 6-TG and 6-MMP levels were associated with leukopenia and hepatotoxicity, respectively. Negligible metabolite levels detected non-compliance as a cause of treatment failure in 2/31 cases. These results indicate that 6-MP metabolite levels predict both clinical responsiveness and drug-related toxicity.

TABLE 1

| Group | n | median 6-TG | 6-TG >225 | median 6-MMP |
|---|---|---|---|---|
| Responders | 58 | 295 | 45/58 (78%) | 3094 |
| Non-responders | 31 | 184* | 8/31 (26%) | 2048 |
| Hepatic toxicity | 7 | 258 | 5/7 | 9211** |
| Pancreatic toxicity | 6 | 211 | 2/6 | 2342 |
| Hematologic toxicity | 6 | 414+ | 5/5 | 7042 | p Values
*<0.001
+<0.03
‡0 < 0.001
**<0.001

These results demonstrate that determining levels of 6-MP metabolites is useful for predicting efficacy and toxicity of 6-MP drug therapy administered to IBD patients.

EXAMPLE II

6-Mercaptopurine Metabolite Levels Correlate with Optimal 6-MP Therapy in IBD Patients This example describes prospective examination of the correlation of 6-MP metabolite levels with therapeutic response to 6-MP drug therapy and 6-MP drug related toxicity in IBD patients treated with 6-MP.

To obtain additional statistical data on IBD patients treated with a 6-MP drug, additional patients and samples were analyzed and combined with the data obtained in Example I. Blood was sampled at least once in 93 IBD patients followed at Sainte-Justine Hospital IBD Center, Montreal, Canada, who were administered 6-MP drug therapy for at least 4 months. The 93 patients were pediatric patients, with 80 diagnosed as having CD, 8 diagnosed as having UC, and 5 diagnosed as having indeterminate colitis (CD or UC). All but 7 patients were given AZA. The dosages were converted to 6-MP equivalents using a factor of 2.07 as described in Example I. For some patients, two or more samples were obtained and analyzed. Response to 6-MP was defined by clinical remission (HBI <5, closed fistula) without corticosteroids. Disease activity and physical exam were ascertained at each clinic visit at which 6-MP metabolite levels were determined (clinical evaluation point). Hematological, pancreatic and hepatic laboratory parameters were evaluated simultaneously. Erythrocyte 6-TG and 6-MMP concentrations (pmol/$8\times10^8$ RBC) were measured by HPLC (Cuffari et al., supra, 1996a).

The results of the analysis of 6-MP metabolites in IBD patients are shown in Table 2. The number of samples corresponds to the number of different samples obtained from the 93 patients. 6-TG quartile analysis, in which values are determined at 25, 50 and 75% of the data set, revealed that the frequency of response significantly increased at levels >230 pmol/$8\times10^8$ RBC (p<0.01). Among patients in relapse, only 28% of patients had 6-TG levels >230 pmol/$8\times10^8$ RBC. In contrast, 65% of patients in remission had 6-TG levels >230 pmol/$8\times10^8$ RBC (p<0.01). Therefore, erythrocyte 6-TG concentrations were significantly and independently associated with therapeutic response to 6-MP drug therapy.

Figure 3:
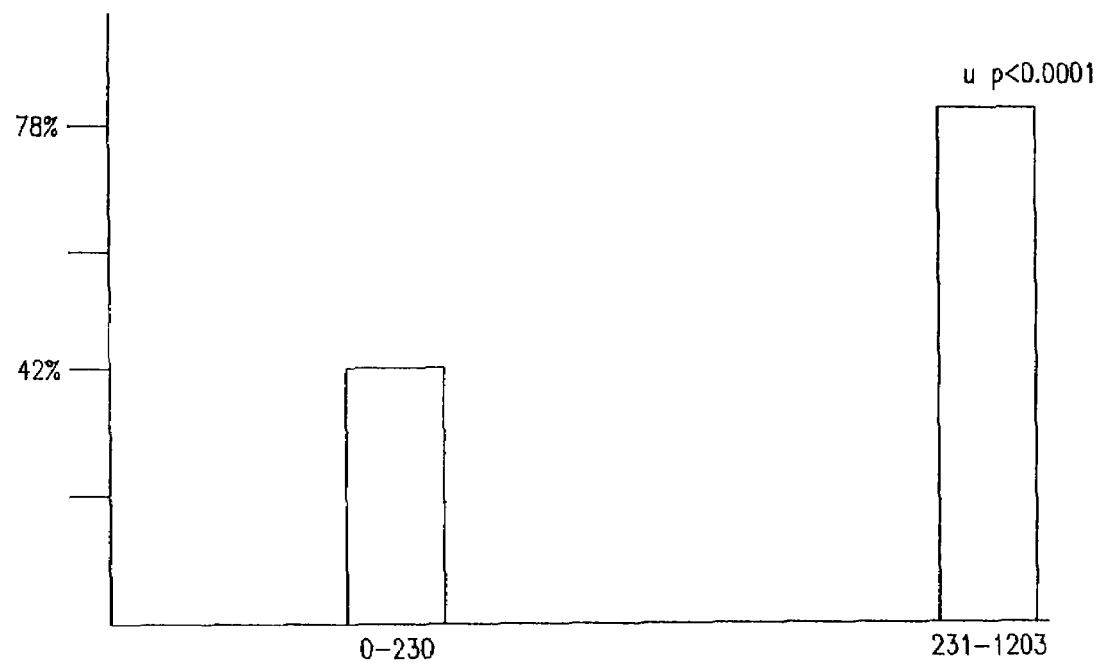
FIG. 3 shows ranges of 6-thioguanine in IBD patients treated with a 6-MP drug.

The induction and maintenance of remission was found to be optimal at 6-TG levels >230 pmol/$8\times10^8$ RBC. 78% of patients above a median 6-TG of 230 pmol/$8\times10^8$ RBC were responders (see FIG. 3). These results indicate that a 6-TG value of 230 pmol/$8\times10^8$ RBC can be used to predict efficacy of drug treatment with a 6-MP drug such as 6-MP or azathioprine.

TABLE 2

| Clinical evaluation point | (n) | Median 6-TG | Median 6-MMP | Median dose (mg/kg/day) |
|---|---|---|---|---|
| Remission | 106 | 309* | 2600 | 1.3 |
| Relapse | 72 | 197 | 1602 | 1.25 |
| *p value | | <0.0001 | 0.3 | 0.4 |

Toxicity in the IBD patients treated with a 6-MP drug was also evaluated. Toxicity was measured essentially as described previously (Cuffari et al., supra, 1996a). Thirty six patients (39%) experienced an adverse event. Hepatotoxicity was observed in 17% of patients, measured as the serum level of alanine aminotransferase (ALT) or aspartate aminotransferase (AST) (ALT, AST; exceeding or greater than 2× upper limit of normal). Leukopenia was observed in 14% of patients (white blood cell (WBC) <4000). Pancreatic toxicity was observed in 7% of patients (lipase/amylase >2×N). High 6-MMP levels correlated significantly with hepatotoxicity (5463 with hepatotoxicity versus 2177 without hepatotoxicity; p=0.04). Leukopenia was observed in only 8% (8/106) of samples from patients in remission, with significantly higher 6-TG levels observed in these patients (mean value of 490 in patients with leukopenia versus mean value of 323 without leukopenia; p<0.04; median values were 342 versus 307, respectively). Therefore, leukopenia did not correlate with therapeutic efficacy. Furthermore, drug dose (per kg) did not correlate with therapeutic efficacy (see Table 2). However, those patients who do develop leukopenia have a higher 6-TG level than the rest of the responder group. These results indicate that 6-TG levels should be monitored to avoid potential clinical bone marrow suppression in responder patients who have high levels of 6-TG.

These results demonstrate a significant correlation between erythrocyte 6-TG levels and the therapeutic response to 6-MP drug treatment in IBD patients. The induction and maintenance of remission was found to be optimal at 6-TG levels >230 pmol/$8\times10^8$ RBC. Therefore, monitoring 6-MP metabolite levels, in particular 6-TG, is useful for determining that a therapeutically effective concentration of 6-MP metabolites is maintained while treating IBD patients with a 6-MP drug. Monitoring 6-MP metabolite levels, in particular 6-TG and 6-MMP, is also useful for minimizing 6-MP drug related toxicity.

EXAMPLE III

Gender and Age Differences in Metabolism of a 6-MP Drug

This example describes gender and age differences observed in pediatric patients treated with 6-MP drug therapy.

Pediatric IBD patients undergoing 6-MP drug therapy were assessed for levels of 6-MP metabolites. These patients were wild type for TPMT. Patients were assessed based on gender and age as it relates to puberty. Puberty is established at 12 years of age in girls and 14 years of age in boys.

As shown in Table 3, the 6-MMP values are much lower in boys after puberty (greater than 14 years). Since the total amount of thiometabolites is lower, this indicates that either lower doses of 6-MP are used or that there is a difference in the bioavailability of 6-MP after puberty in males.

TABLE 3

6-MP Metabolite Levels in Pediatric IBD Patients

| | Number Observed | 6-TG level (pmol per $8 \times 10^8$ RBC) | 6-MMP level (pmol per $8 \times 10^8$ RBC) | Ratio 6-MMP/6-TG |
|---|---|---|---|---|
| Girls (0-12 y) | 39 | 182.2 | 3447.0 | 18.52 |
| Girls (>12 y) | 116 | 217.2 | 3304.5 | 12.55 |
| Boys (0-14 y) | 51 | 235.0 | 3681.6 | 17.24 |
| Boys (>14 y) | 104 | 222.5 | 1662.3* | 6.78* |

*$p < 0.001$

These results demonstrate that gender and age can affect the metabolism of 6-MP in pediatric IBD patients undergoing 6-MP drug therapy.

EXAMPLE IV

Thiopurine Methyltransferase (TPMT) Genotyping and Responsiveness to 6-MP Drug Therapy This example describes TPMT genotyping of IBD patients treated with 6-MP drug therapy.

The genotype of TPMT was determined in IBD patients that were responders and non responders. Genotyping of TPMT was measured essentially as described previously (Baccichet et al., *Leuk. Res.* 21:817-823 (1997); Zietkiewicz et al., *Gene* 205:161-171 (1997)). The data shown in Table 4 indicate that patients heterozygous for the TPMT mutation had significantly higher 6-TG levels compared to those patients without the mutation. All heterozygote patients were responders to 6-MP.

TABLE 4

TPMT Genotyping of IBD Patients

| | Heterozygote | Normal |
|---|---|---|
| Responder | 100% | 55% |
| Non responder | 0% | 45% |
| mean 6-TG | 589* | 247 | p value
*less than 0.0001

TPMT genotyping revealed that 8 of 93 (9%) of patients were heterozygotes. No homozygous TPMT deficient patients were detected. All 8 heterozygotes responded to 6-MP and had 6-TG levels >230 pmol/$8 \times 10^8$ RBC.

These results demonstrate that TPMT genotyping is useful for predicting the effectiveness of 6-MP therapy in an IBD patient. Heterozygote patients are expected to have lower TPMT activity and should therefore be monitored for high levels of 6-TG for possible toxic levels associated with leukopenia or bone marrow suppression. 6-MP drug doses can be reduced accordingly. Wild type homozygous patients are expected to have higher TPMT activity and should therefore be monitored to maintain an effective therapeutic level of 6-TG and to determine if patients develop toxic levels of 6-MMP. Homozygous patients deficient in TPMT activity can be treated with lower doses of a 6-MP drug provided that patients are closely monitored for toxicity such as leukopenia.

All journal articles and references provided herein, in parenthesis or otherwise, are incorporated herein by reference.

Although the invention has been described with reference to the examples provided above, it should be understood that various modifications can be made without departing from the spirit of the invention. Accordingly, the invention is limited only by the claims.

The invention claimed is:

1. An assay method for monitoring 6-thioguanine levels in a subject receiving azathioprine or 6-mercaptopurine, said method comprising:
    (a) determining a level of 6-thioguanine present in said subject from red blood cells; and
    (b) indicating that said determined level of 6-thioguanine is associated with a higher likelihood of response when said determined level of 6-thioguanine is between about 230 pmol per $8 \times 10^8$ red blood cells and about 450 pmol per $8 \times 10^8$ red blood cells.

2. The method of claim 1, wherein said subject has a disease or disorder selected from the group consisting of an immune-mediated gastrointestinal disorder and a non-IBD autoimmune disease.

3. The method of claim 2, wherein said immune-mediated gastrointestinal disorder is Crohn's disease or ulcerative colitis.

4. The method of claim 1, wherein said level of 6-thioguanine is determined using high pressure liquid chromatography.

5. The method of claim 1, wherein said subject is receiving azathioprine.

6. An assay method for monitoring 6-thioguanine levels in a subject receiving azathioprine or 6-mercaptopurine, said method comprising:
    (a) determining a level of 6-thioguanine present in said subject from red blood cells; and
    (b) indicating that said determined level of 6-thioguanine is associated with a higher likelihood of response when said determined level of 6-thioguanine is between about 230 pmol per $8 \times 10^8$ red blood cells and about 400 pmol per $8 \times 10^8$ red blood cells.

7. The method of claim 6, wherein said subject has a disease or disorder selected from the group consisting of an immune-mediated gastrointestinal disorder and a non-IBD autoimmune disease.

8. The method of claim 7, wherein said immune-mediated gastrointestinal disorder is Crohn's disease or ulcerative colitis.

9. The method of claim 6, wherein said level of 6-thioguanine is determined using high pressure liquid chromatography.

10. The method of claim 6, wherein said subject is receiving azathioprine.

11. An assay method for monitoring 6-thioguanine levels in a subject receiving azathioprine or 6-mercaptopurine, said method comprising:
    (a) determining a level of 6-thioguanine present in said subject from red blood cells; and
    (b) indicating that said determined level of 6-thioguanine is associated with a higher likelihood of response when said determined level of 6-thioguanine is between about 260 pmol per $8 \times 10^8$ red blood cells and about 450 pmol per $8 \times 10^8$ red blood cells.

12. The method of claim 11, wherein said subject has a disease or disorder selected from the group consisting of an immune-mediated gastrointestinal disorder and a non-IBD autoimmune disease.

13. The method of claim 12, wherein said immune-mediated gastrointestinal disorder is Crohn's disease or ulcerative colitis.

14. The method of claim 11, wherein said level of 6-thioguanine is determined using high pressure liquid chromatography.

15. The method of claim 11, wherein said subject is receiving azathioprine.

16. An assay method for monitoring 6-thioguanine levels in a subject receiving azathioprine or 6-mercaptopurine, said method comprising:
    (a) determining a level of 6-thioguanine present in said subject from red blood cells; and
    (b) indicating that said determined level of 6-thioguanine is associated with a higher likelihood of response when said determined level of 6-thioguanine is between about 260 pmol per $8 \times 10^8$ red blood cells and about 400 pmol per $8 \times 10^8$ red blood cells.

17. The method of claim 16, wherein said subject has a disease or disorder selected from the group consisting of an immune-mediated gastrointestinal disorder and a non-IBD autoimmune disease.

18. The method of claim 17, wherein said immune-mediated gastrointestinal disorder is Crohn's disease or ulcerative colitis.

19. The method of claim 16, wherein said level of 6-thioguanine is determined using high pressure liquid chromatography.

20. The method of claim 16, wherein said subject is receiving azathioprine.

21. An assay method for monitoring 6-thioguanine levels in a subject receiving azathioprine or 6-mercaptopurine, said method comprising:
    (a) determining a level of 6-thioguanine present in said subject from red blood cells;
    (b) indicating that said determined level of 6-thioguanine is associated with a lower likelihood of response when said determined level of 6-thioguanine is less than about 230 pmol per $8 \times 10^8$ red blood cells; and
    (c) indicating that said determined level of 6-thioguanine is associated with a higher risk of toxicity when said determined level of 6-thioguanine is greater than about 450 pmol per $8 \times 10^8$ red blood cells.

22. The method of claim 21, wherein said subject has a disease or disorder selected from the group consisting of an immune-mediated gastrointestinal disorder and a non-IBD autoimmune disease.

23. The method of claim 22, wherein said immune-mediated gastrointestinal disorder is Crohn's disease or ulcerative colitis.

24. The method of claim 21, wherein said level of 6-thioguanine is determined using high pressure liquid chromatography.

25. The method of claim 21, wherein said subject is receiving azathioprine.

26. An assay method for monitoring 6-thioguanine levels in a subject receiving azathioprine or 6-mercaptopurine, said method comprising:
    (a) determining a level of 6-thioguanine present in said subject from red blood cells;
    (b) indicating that said determined level of 6-thioguanine is associated with a lower likelihood of response when said determined level of 6-thioguanine is less than about 230 pmol per $8 \times 10^8$ red blood cells; and
    (c) indicating that said determined level of 6-thioguanine is associated with a higher risk of toxicity when said determined level of 6-thioguanine is greater than about 400 pmol per $8 \times 10^8$ red blood cells.

27. The method of claim 26, wherein said subject has a disease or disorder selected from the group consisting of an immune-mediated gastrointestinal disorder and a non-IBD autoimmune disease.

28. The method of claim 27, wherein said immune-mediated gastrointestinal disorder is Crohn's disease or ulcerative colitis.

29. The method of claim 26, wherein said level of 6-thioguanine is determined using high pressure liquid chromatography.

30. The method of claim 26, wherein said subject is receiving azathioprine.

31. An assay method for monitoring 6-thioguanine levels in a subject receiving azathioprine or 6-mercaptopurine, said method comprising:
    (a) determining a level of 6-thioguanine present in said subject from red blood cells;
    (b) indicating that said determined level of 6-thioguanine is associated with a lower likelihood of response when said determined level of 6-thioguanine is less than about 260 pmol per $8 \times 10^8$ red blood cells; and
    (c) indicating that said determined level of 6-thioguanine is associated with a higher risk of toxicity when said determined level of 6-thioguanine is greater than about 450 pmol per $8 \times 10^8$ red blood cells.

32. The method of claim 31, wherein said subject has a disease or disorder selected from the group consisting of an immune-mediated gastrointestinal disorder and a non-IBD autoimmune disease.

33. The method of claim 32, wherein said immune-mediated gastrointestinal disorder is Crohn's disease or ulcerative colitis.

34. The method of claim 31, wherein said level of 6-thioguanine is determined using high pressure liquid chromatography.

35. The method of claim 31, wherein said subject is receiving azathioprine.

36. An assay method for monitoring 6-thioguanine levels in a subject receiving azathioprine or 6-mercaptopurine, said method comprising:
    (a) determining a level of 6-thioguanine present in said subject from red blood cells;
    (b) indicating that said determined level of 6-thioguanine is associated with a lower likelihood of response when said determined level of 6-thioguanine is less than about 260 pmol per $8 \times 10^8$ red blood cells; and
    (c) indicating that said determined level of 6-thioguanine is associated with a higher risk of toxicity when said determined level of 6-thioguanine is greater than about 400 pmol per $8 \times 10^8$ red blood cells.

37. The method of claim 36, wherein said subject has a disease or disorder selected from the group consisting of an immune-mediated gastrointestinal disorder and a non-IBD autoimmune disease.

38. The method of claim 37, wherein said immune-mediated gastrointestinal disorder is Crohn's disease or ulcerative colitis.

39. The method of claim 36, wherein said level of 6-thioguanine is determined using high pressure liquid chromatography.

40. The method of claim 36, wherein said subject is receiving azathioprine.

41. An assay method for monitoring 6-thioguanine levels in a subject receiving azathioprine or 6-mercaptopurine, said method comprising:

(a) determining a level of 6-thioguanine present in said subject from leukocytes;
(b) corresponding said determined level of 6-thioguanine to a red blood cell level; and
(c) indicating that said determined level of 6-thioguanine is associated with a higher likelihood of response when said corresponded level of 6-thioguanine is between about 230 pmol per $8\times10^8$ red blood cells and about 400 pmol per $8\times10^8$ red blood cells.

42. The method of claim 41, wherein said subject has a disease or disorder selected from the group consisting of an immune-mediated gastrointestinal disorder and a non-IBD autoimmune disease.

43. The method of claim 42, wherein said immune-mediated gastrointestinal disorder is Crohn's disease or ulcerative colitis.

44. The method of claim 41, wherein said level of 6-thioguanine is determined using high pressure liquid chromatography.

45. The method of claim 41, wherein said subject is receiving azathioprine.

* * * * *